United States Patent [19]
Umemura et al.

[11] Patent Number: 4,902,503
[45] Date of Patent: Feb. 20, 1990

[54] ANTIMICROBIAL LATEX COMPOSITION

[75] Inventors: Yoshihiro Umemura; Yasuhiko Ozaki; Akihito Kawaide, all of Kyoto, Japan

[73] Assignee: Unitika Ltd., Hyogo, Japan

[21] Appl. No.: 275,307

[22] Filed: Nov. 23, 1988

[30] Foreign Application Priority Data

Nov. 25, 1987 [JP] Japan ................................ 62-297106
Nov. 25, 1987 [JP] Japan ................................ 62-297108

[51] Int. Cl.$^4$ ................... A61K 31/745; A61K 31/74; A61K 31/78; A01N 55/02
[52] U.S. Cl. ......................................... 424/83; 424/78; 424/81; 514/6; 514/184; 604/265
[58] Field of Search ...................... 424/78, 132, 81, 83; 514/6, 184; 604/265

[56] References Cited

U.S. PATENT DOCUMENTS 2,785,153 3/1957 Locke ...................................... 514/6
4,054,139 10/1977 Crossley ................................ 604/265
4,592,920 6/1986 Murtfeldt ............................. 604/265
4,603,152 7/1986 Laurin et al. ........................ 604/265

FOREIGN PATENT DOCUMENTS 0141628 5/1985 European Pat. Off. .............. 424/78
WO86/02006 4/1986 PCT Int'l Appl. ................. 604/265

OTHER PUBLICATIONS

The Merck Index, vol. 10, 1983, pp. 1223-1224, No. 8363 "Silver Protein, Strong".

Primary Examiner—Joseph L. Schofer
Assistant Examiner—Carmen B. Pili-Curtis
Attorney, Agent, or Firm—Sughrue, Mion, Zinn, Macpeak & Seas

[57] ABSTRACT

A first antimicrobial latex composition comprising a homogeneous blend of a natural rubber latex or a synthetic polymer latex and protein silver and a second antimicrobial latex composition comprising a homogeneous blend of a cationic natural rubber latex or a cationic synthetic polymer latex and a water-soluble silver compound, wherein each antimicrobial latex composition exhibits excellent long term stability during storage and can be readily prepared.

14 Claims, No Drawings

ANTIMICROBIAL LATEX COMPOSITION

FIELD OF THE INVENTION

This invention relates to an antimicrobial latex composition. More particularly, it relates to an antimicrobial latex composition suitable for the production of latex products such as medical devices, sanitary goods, devices for producing foods and ice pillows, each having a sustained antimicrobial activity.

BACKGROUND OF THE INVENTION

Medical devices and sanitary goods that are not disposable should be disinfected or sterilized prior to the use in order to achieve their intended purpose. However, it is frequently observed that a medical device employed for a prolonged period of time does not sustain aseptic properties. Thus, it has been desired to overcome this problem.

The most effective solution to this problem has been to produce a medical device of which the surface contains a definite amount of an antimicrobial agent which is present throughout the use of the device. When such a device is prepared from a latex, it is required that the antimicrobial agent is homogeneously and stably blended with the latex which is then formed into the intended medical device.

It is known that heavy metals such as gold, silver, copper and zinc as well as compounds thereof exert an intense antimicrobial effect on a wide spectrum of microorganisms including various bacteria and fungi at extremely low concentrations of each metal ion. This effect is called an oligodynamic effect.

U.S. Pat. Nos. 4,483,688, 4,592,920, 4,603,152 and 4,054,139 disclose producing a medical device having an antimicrobial activity by taking advantage of the oligodynamic effect of these metals or compounds thereof. Namely, these metals or compounds thereof are dispersed in a matrix material which is then molded or used as a coating to produce the devices.

U.S. Pat. No. 4,483,688 discloses a catheter prepared by dispersing a fine metal powder such as silver powder in an appropriate binder and then coating a catheter with the same. However, this method is somewhat disadvantageous in the lack of complete dispersibility of said fine metal powder in the binder.

U.S. Pat. No. 4,592,920 discloses an antimicrobial catheter prepared by grinding an antimicrobial metal compound such as silver oxide to give a particle size of 30 $\mu$m or less and dispersing the oxide in a suspension such as a latex or polyurethane which can then be hardened and formulated into a catheter. However, it is required in this case to add a surfactant to prevent the reaggregation of the metal compound particles during the grinding step as well as thereafter to maintain these particles in a stable state.

U.S. Pat. No. 4,603,152 discloses blending silver nitrate or silver oxide with a natural or synthetic rubber latex. In the Example 13 of this patent, a natural rubber latex is blended with powdery silver oxide. However, the dispersion of the powdery silver oxide in the highly viscous latex requires an undue prolonged period of time. Further, the addition must be carried out in a complex manner.

Further, U.S. Pat. No. 4,054,139 discloses coating the surface of a catheter with a polymer latex containing a silver compound such as silver nitrate. However, this method is disadvantageous in that the stability of the coating solution comprising the latex and the silver compound is poor, because the addition of silver nitrate to a latex causes to easily aggregate in the mixture. Thus, it is difficult to produce the coated catheter in a continuous manner.

In order to produce an antimicrobial medical device on an industrial scale, a suspension containing an antimicrobial agent and a mixture comprising a polymer which serves as a matrix, the antimicrobial agent and a solvent must remain stable during long term storage.

In general, metal compounds, especially silver compounds, are hardly soluble in water. When a silver compound is blended with a latex in the form of a solution, the silver concentration in the matrix material is extremely low. Thus, the required antimicrobial activity cannot be obtained in this case.

On the other hand, a latex such as a natural rubber latex dispersed in water is a highly unstable system. Thus, it gels even with a slight change in environmental factors such as pH or temperature. When an aqueous solution containing a silver compound such as silver nitrate which is highly soluble water is added to a latex at a high concentration in order to give a high silver concentration in a matrix material, silver nitrate would break the system wherein the latex suspended in the aqueous solution in a stable form. When silver carbonate which has an extremely low solubility in water is added, the stable latex dispersion system is also broken and aggregation is observed. Therefore, it has been impossible to obtain a stable latex composition.

Accordingly, a specific technique is required in order to prevent a stable latex dispersion system from breakage when a silver compound is dispersed in the latex and blended therewith.

SUMMARY OF THE INVENTION

It is a first object of the present invention to provide an antimicrobial latex composition suitable for the production of latex products having a sustained antimicrobial activity.

It is a second object of the present invention to provide an antimicrobial homogeneous latex composition which contains a large amount of silver.

Further, it is a third object of the present invention to provide an antimicrobial latex composition which remains stable for a prolonged period of time without the necessity of adding any surfactant to homogeneously and stably disperse an antimicrobial agent.

Further, it is yet another object of the present invention to provide an antimicrobial latex composition which can be easily prepared and which remains stable for a prolonged period of time.

To obtain the above-mentioned antimicrobial latex composition, the present inventors have conducted extensive studies, and as a result, found that these objects can be achieved by blending protein silver having a high solubility in water with a natural rubber latex or a synthetic polymer latex.

Accordingly, the crux of the present invention resides in an antimicrobial latex composition prepared by blending silver protein with a natural rubber latex or a synthetic polymer latex, and in an antimicrobial latex composition prepared by blending water-soluble silver compound with a cationic natural rubber latex or a cationic synthetic polymer latex.

DETAILED DESCRIPTION OF THE INVENTION

Now the present invention will be described in detail.

In the present invention, the term a natural rubber latex includes common ones such as anionic natural rubber latexes and cationic natural rubber latexes, unless otherwise noted. On the other hand, a synthetic polymer latex represents a latex comprising a synthetic polymer and which is an anionic synthetic polymer latex or a cationic synthetic polymer latex, unless otherwise noted.

The common natural rubber latex such as Soctex and Asiatex available from Socfin Company Berhad and Plantation Latex Berhad, respectively, to be used in the present invention is a latex comprising an aqueous solution, which flows from the cortex of a rubber plant and contains various organic and inorganic materials, as a disperse medium and the rubber content as a dispersant optionally together with one or more various additives such as a pH adjustor, curing agent, curing accelerator, softening agent, bulking agent, antioxidant and colorant. This latex, which usually contains about 0.3% by weight of ammonia as a pH adjustor, is an anionic latex having a pH value adjusted to be from about 8 to 11, preferably from about 9 to 11.

The cationic natural rubber latex to be used in the present invention is a so-called acidic latex which has a pH value between about 1 and 5, preferably between about 1.5 and 4.7 (the isoelectric point of the protein serving as a protective colloid), and more preferably between about 2 and 3. In this type of latex, rubber particles are positively charged, contrary to those in a common natural rubber latex, and are stabilized by mutual repulsion. Such an acidic latex may be prepared by, for example, adding a cationic or nonionic surfactant to the above-mentioned natural rubber latex (solids content: 20 to 70% by weight, pH 9 to 11) at a ratio of from 1 to 5% by weight of the former based on the rubber content and then adjusting the pH value to be below 3 by adding an appropriate inorganic or organic acid thereto. Conventional application of such an acidic latex had been limited to specific purposes, for example, the treatment of negatively charged fiber or paper or the preparation of derivatives such as rubber hydrochloride, chlorinated rubber or reduced rubber directly from a latex. Thus, there had never been known an acid latex blended with a silver compound as the one proposed by the present invention.

The synthetic polymer latex used in the present invention comprises polymer(s), for example, homopolymers and copolymers of vinyl monomers such as ethylene, styrene, vinyl acetate, vinyl chloride, vinylidiene chloride, acrylonitrile, (meth)acrylate, vinylpyridine and methyl vinyl ether; homopolymers and copolymers of diene monomers such as butadiene, isoprene, 1,3-pentadiene, 1,5-hexadiene, 1,6-heptadiene and chloroprene; copolymers of the above-mentioned vinyl monomers and diene monomers; and copolymers of vinyl monomers having functional group(s) such as epoxide, amino, carboxymethyl, acid anhydride, hydroxyl, amino, N-methylolamido and isocyanate groups with the above-mentioned monomers; as the main component optionally together with various additives such as a surfactant, crosslinking agent, bulking agent and softening agent. Such a synthetic polymer latex as defined above, for example, acrylonitrile-butadiene copolymer latex (pH 9.5, Nipol 1562, mfd. by Nippon Zeon Co., Ltd.) and chloroprene latex (pH 10.2, LM-50, mfd. by Denki Kagaku Kogyo K.K.), is usually used as an anionic system. Further, a cationic synthetic polymer latex comprising the above-mentioned polymer(s) as the main component together with a cationic surfactant as an emulsifying and dispersing agent may be used in the present invention. This cationic synthetic polymer latex may further contain, for example, a nonionic surfactant, crosslinking agent, bulking agent and softening agent, if required.

In the present invention, protein silver is employed as an antimicrobial agent. Protein silver is a compound comprising protein and silver as described, for example, in *The Merk Index*, 10th ed., pp. 1223–1224, No. 8363 (1983). It is preferable that the protein silver contains from 7.5 to 8.5% by weight of silver according to *The Pharmacopoeia of Japan*.

The content of the protein silver varies depending on the purpose. In general, it is preferred that the content of silver based on the solids content of the latex ranges from about 0.1 to 10% by weight, and more preferably from about 0.5 to 5% by weight. A content of silver exceeding 10% by weight might lower the strength of latex products produced therefrom. When it is less than 0.1% by weight, on the other hand, the antimicrobial effect achieved is unsatisfactory.

When the protein silver is blended with the latex, the solid content of the latex varies depending on the purpose, namely, whether the resulting composition is molded to produce, for example, a medical device, or it is used as a coating. It is recommended that the solid content of the latex is from about 20 to 70% by weight, in general, preferably from about 30 to 65% by weight, more preferably from about 40 to 60% by weight. The latex may have any pH value ranging from the alkaline to the acidic range.

The antimicrobial latex composition of the present invention may be prepared virtually by any process so long as all components are homogeneously blended with each other. Thus, various known processes are available therefor. For example, it is preferable to directly add an aqueous solution of protein silver, more preferably one which has a high protein silver concentration, to a latex.

When a cationic natural rubber latex or a cationic synthetic polymer latex is used, a water-soluble silver compound other than protein silver may be blended therewith.

Examples of appropriate silver compounds include silver salts which are formed by reacting silver with an inorganic or organic acid. Preferred examples of the silver salts include silver nitrate, silver lactate, silver chlorate, silver fluoride and silver picrate.

The expression "water-soluble" as used herein means having a solubility of 1.0 g or above, preferably 5.0 g or above, in 100 g of distilled water at 20° C.

The preferred amount of the water-soluble silver compound blended varies depending on the purpose and the employed silver compound. It is preferred to use from about 0.1 to 30% by weight, more preferred from about 0.5 to 10% by weight, (in terms of silver) of the silver compound based on the solid content of the latex. When silver nitrate is used as the silver compound, a high silver content can be obtained by the use of smaller amount thereof as compared with the other compounds.

A content of the blended silver exceeding 30% by weight might lower the strength of molded products or films obtained therefrom. When it is less than 0.1% by weight, on the other hand, the intended antimicrobial effect is not obtained.

When the above-mentioned silver compound is used as an antimicrobial agent, an acidic latex having a pH value between about 1 and 5, preferably between about 1.5 and 4.7 (the isoelectric point of the protein serving as a protective colloid), and more preferably between about 2 and 3, may be employed as a cationic natural rubber latex.

In addition, a cationic synthetic polymer latex having a pH value of from about 1 to 5 may be used.

The solid content of the above-mentioned cationic natural rubber latex or cationic synthetic polymer latex varies depending on the purpose, namely, whether the resulting antimicrobial latex composition is molded into a medical device and the like, or it is used as a coating, similar to the case of the protein silver. A solid content of from about 20 to 70% by weight is general.

This antimicrobial latex composition may be prepared by virtually any known method as in the case of the protein silver. For example, an aqueous solution of a water-soluble silver compound, particularly that having a high concentration of the water-soluble silver compound, may be directly added to a latex.

The antimicrobial latex composition of the present invention homogeneously contains silver and remains stable for a long period of time. In addition, it can be easily prepared.

Thus, the antimicrobial latex composition of the present invention can be suitably used, for example, in the production of latex products requiring a sustained antimicrobial activity upon prolonged use, such as medical devices, sanitary goods, and devices for producing food or ice pillows. Examples of these latex products include various catheters such as urine catheters, bags such as stercus bags, supplying/drainage tubes, sponges, rubberized fabrics such as bed sheets and diaper covers, bath mats, sizing agents for paper, binders for nonwoven fabric, paintings and adhesives.

The present invention is illustrated in greater detail with reference to the following Examples and Comparative Examples, but it is understood that the present invention is not deemed to be limited thereto. In these examples, all the parts are by weight unless otherwise indicated.

EXAMPLE 1

0.3 part of zinc dimethyldithiocarbamate, 1.5 parts of sulfur, 3 parts of zinc oxide and 1.2 parts of stearic acid were homogeneously dispersed in 100 parts of a natural rubber latex (pH 10.7) having a solids content of approximately 50% by weight. The latex blend obtained is hereinafter referred to as solution A. Separately, 6.4 parts of protein silver were dissolved in 20 parts of distilled water and the resulting solution was added to 100 parts of solution A while stirring. Thus, a latex composition (silver content: 1% by weight) wherein the protein silver was homogeneously dispersed was obtained.

This latex composition was casted onto a glass plate and dried at room temperature. Then, it was cured at 70° to 80° C. for approximately ten hours to form a sheet.

The antimicrobial activity of the obtained sheet was determined in the following manner.

The sheet was cut and a piece thereof was washed with a 70% aqueous solution of ethanol under aseptic conditions. After drying and distilling off the ethanol, the sheet piece was placed onto the bottom of a sample vial. Then, 200 μl of a culture liquor obtained by incubating Escherichia coli at 37° C. overnight in a Trypticase ® Soy Broth (mfd. by BBL Microbiology Systems Vecton Dickinson & Co.) medium was placed thereon. After sealing the vial, the bacteria were cultured at 37° C. for 18 hours. Subsequently, the culture liquor was collected by adding physiological saline solution containing 0.1% of a surfactant (Tween 80 mfd. by Yamakei Sangyo K.K.) to the vial. Then, surviving cells therein were counted according to the colony counting method. The above procedure was repeated except that the culture liquor was directly placed onto the bottom of the vial to thereby give a control case.

As a result, the bacterial count of the test case corresponded to 1.3% of that of the control case.

The latex of Example 1 was then allowed to stand at room temperature for one week. It remained stable without showing any increase in viscosity or aggregation.

EXAMPLE 2

6.4 parts of protein silver dissolved in 20 parts of distilled water were added while stirring to 100 parts of an anionic styrene/butadiene copolymer latex (pH 9.5) having a solids content of approximately 50% by weight. Thus, a latex composition (silver content: 1% by weight) wherein the protein silver was homogeneously dispersed was obtained.

With the use of this latex composition, a sheet was formed in the same manner as the sheet described in Example 1.

The antimicrobial activity of the sheet obtained was determined in the same manner as the sheet of Example 1. The bacterial count of the test case corresponded to 6.5% of that of the control case.

The latex of Example 2 was then allowed to stand at room temperature for one month. It remained stable without showing any increase in viscosity or aggregation.

EXAMPLE 3

Five parts of protein silver dissolved in 15 parts of distilled water were added while stirring to 100 parts of an anionic acrylonitrile/butadiene copolymer latex (pH 9.5, Nipol 1562, mfd. by Nippon Zeon Co., Ltd. having a solids content of approximately 40% by weight. Thus, a latex composition (silver content: 1% by weight) wherein the protein silver was homogeneously dispersed was obtained.

With the use of this latex composition, a sheet was formed in the same manner as the sheet described in Example 1.

The antimicrobial activity of the sheet obtained was determined in the same manner as the sheet of Example 1. The bacterial count of the test case corresponded to 3.5% of that of the control case.

The latex of Example 3 was then allowed to stand at room temperature for one week. It remained stable without showing any increase in viscosity or aggregation.

EXAMPLE 4

Six parts of protein silver dissolved in 18 parts of distilled water were added while stirring to 100 parts of an anionic chloroprene latex (pH 10.2, LM-50, mfd. by Denki Kagaku Kogyo Kabushiki Kaisha) having a solids content of approximately 50% by weight. Thus, a latex composition (silver content: 1% by weight) wherein the protein silver was homogeneously disposed was obtained.

With the use of this latex composition, a sheet was formed in the same manner as the sheet described in Example 1.

The antimicrobial activity of the sheet obtained was determined in the same manner as the sheet of Example 1. The bacterial count of the test case corresponded to 4.5% of that of the control case.

The latex of Example 4 was then allowed to stand at room temperature for one week. It remained stable without showing any increase in viscosity or aggregation.

EXAMPLE 5

30 parts of protein silver dissolved in 70 parts of distilled water were added while stirring to 100 parts of solution A prepared in Example 1. Thus, a latex composition (silver content: 5% by weight) wherein the protein silver was homogeneously dispersed was obtained.

With the use of this latex composition, a sheet was formed in the same manner as the sheet described in Example 1.

The antimicrobial activity of the sheet was determined in the same manner as the sheet of Example 1. The bacterial count of the test case corresponded to 8% of that of the control case.

The latex of Example 5 was then allowed to stand at room temperature for two months. It remained stable without showing any increase in viscosity or aggregation.

EXAMPLE 6

12 parts of a nonionic surfactant aqueous solution (10% by weight) were added to 100 parts of Sectex (mfd. by Socfin Company) while stirring. The resulting latex was adjusted to pH 2.5 by adding 8 parts of aqueous hydrochloride solution.

0.3 parts of zinc dimethyldithiocarbamate, 1.3 parts of sulfur, 2.8 parts of zinc oxide and 1.2 parts of stearic acid were homogeneously dispersed in 100 parts of the acidic natural rubber latex having a solids content of approximately 50% by weight. Thus, a latex blend containing natural rubber as the main component, which is referred to as solution B hereinafter, was obtained. Six parts of protein silver dissolved in 20 parts of distilled water were added while stirring to 100 parts of this latex blend. Thus, a latex composition (silver content: 1% by weight) wherein the protein silver was homogeneously dispersed was obtained.

With the use of this latex composition, a sheet was formed in the same manner as the sheet described in Example 1.

The antimicrobial activity of the sheet obtained was determined in the same manner as the sheet of Example 1. The bacterial count of the test case corresponded to 0.8% of that of the control case.

The latex composition of Example 6 was then allowed to stand at room temperature for one week. It remained stable without showing any increase in viscosity or aggregation.

EXAMPLE 7

23 parts of protein silver dissolved in 60 parts of distilled water were added while stirring to 100 parts of the latex composition prepared in Example 6. Thus, a latex composition (silver content: 4% by weight) wherein the protein silver was homogeneously dispersed was obtained.

With the use of this latex composition, a sheet was formed in the same manner as the sheet described in Example 1.

The antimicrobial activity of the sheet obtained was determined in the same manner as the sheet of Example 1. The bacterial count of the test case corresponded to 5.2% of that of the control case.

The latex of Example 7 was then allowed to stand at room temperature for one month. It remained stable without showing any increase in viscosity or aggregation.

COMPARATIVE EXAMPLE 1

5 parts of a silver nitrate aqueous solution (10% by weight) was added under stirring to 100 parts of solution A used in Example 1. The latex blend showed a rapid increase in viscosity and formed a number of small aggregates. A homogeneous sheet could not be formed therefrom.

COMPARATIVE EXAMPLE 2

5 parts of a silver nitrate aqueous solution (10% by weight) was added under stirring to 100 parts of the anionic acrylonitrile/butadiene copolymer latex composition used in Example 3. Aggregates were formed in the latex and a homogeneous sheet could not be formed therefrom.

COMPARATIVE EXAMPLE 3

10 parts of a silver carbonate suspended aqueous solution (10% by weight) were added to 100 parts of an anionic natural rubber latex (pH 10.0) which is defined as solution A in Example 1. After one day, the latex blend formed a number of small aggregates. A homogeneous sheet was not formed therefrom.

EXAMPLE 8

Five parts of a silver nitrate aqueous solution (10% by weight) were added to 100 parts of the above solution B used in Example 6 while stirring. The latex formed showed no aggregation and a latex composition (silver content: 0.6% by weight) wherein the silver nitrate was homogeneously dispersed was obtained.

This latex composition was casted onto a glass plate and dried at room temperature. Then, it was cured at from 70° to 80° C. for approximately ten hours to form a sheet.

The antimicrobial activity of the sheet was determined in the following manner.

The sheet was cut and a piece thereof was washed with a 70% aqueous solution of ethanol under aseptic conditions. After drying and distilling off the ethanol, the sheet piece was placed onto the bottom of a sample vial. Then, 200 μl of a culture liquor obtained by incubating Escherichia coli at 37° C. overnight in a Tripticase® Soy Broth medium was placed thereon. After sealing the vial, the bacteria were cultured at 37° C. for 18 hours. Subsequently, the culture liquor was collected by adding physiological saline solution containing 0.1% of a surfactant (Tween 80 mfd. by Yamakei Sangyo K.K.) to the vial. Then, surviving cells therein were counted according to the colony counting method. The above procedure was repeated except that the culture liquor was directly placed onto the bottom of the vial to thereby give a control case.

As a result, the bacterial count of the test case corresponded to 0.7% of that of the control case.

The latex of Example 8 was then allowed to stand at room temperature for one week. It remained stable without showing any increase in viscosity or aggregation.

EXAMPLE 9

Three parts of an aqueous solution of silver nitrate (10% by weight) were added while stirring to 100 parts of an acidic chloroprene latex (pH 2.5) having a solids content of approximately 40% by weight. Thus, a latex composition (silver content: 0.5% by weight) wherein the silver nitrate was homogeneously dispersed was obtained.

With the use of this latex composition, a sheet was formed in the same manner as the sheet described in Example 8.

The antimicrobial activity of the sheet obtained was determined in the same manner as the sheet of Example 8. The bacterial count of the test case corresponded to 10.3% of that of the control case.

The latex of Example 9 was then allowed to stand at room temperature for one week. It remained stable without showing any increase in viscosity or aggregation.

EXAMPLE 10

25 parts of an aqueous solution of silver nitrate (30% by weight) were added to 100 parts of solution B prepared in Example 8 while stirring. The latex showed no aggregation and a latex composition (silver content: 9.5% by weight) wherein the silver nitrate was homogeneously dispersed was obtained.

This latex composition was then allowed to stand at room temperature for one month. It remained stable without showing any increase in viscosity or aggregation.

With the use of this latex composition, a sheet was formed in the same manner as the sheet described in Example 8.

The antimicrobial activity of the sheet obtained was determined in the same manner as the sheet described in Example 8. The bacterial count of the test case corresponded to 1.3% of that of the control case.

While the invention has been described in detail and with reference to specific embodiments thereof, it will be apparent to one skilled in the art that various changes and modifications can be made therein without departing from the spirit and scope thereof.

What is claimed is:

1. An antimicrobial latex composition comprising a homogeneous mixture of a natural rubber latex or a synthetic polymer latex and protein silver.

2. An antimicrobial latex composition according to claim 1, wherein said natural rubber latex or said synthetic polymer latex has solids content of about 20 to 70% by weight.

3. An antimicrobial latex composition according to claim 2, wherein said natural rubber latex or said synthetic polymer latex has solids content of about 30 to 65% by weight.

4. An antimicrobial latex composition according to claim 1, wherein said protein silver is present in an amount of about 0.1 to 10% by weight, in terms of silver, based on the solids content of said latex.

5. An antimicrobial latex composition according to claim 4, wherein said protein silver is present in an amount of about 0.5 to 5% by weight, in terms of silver, based on the solids content of said latex.

6. An antimicrobial latex composition according to claim 1, wherein said latex is an anionic rubber latex and has a pH value of from about 8 to 11.

7. An antimicrobial latex composition according to claim 1, wherein said latex is a cationic rubber latex and has a pH value of from about 1 to 5.

8. An antimicrobial latex composition comprising a homogeneous mixture of a cationic natural rubber latex or a cationic synthetic polymer latex and a water-soluble silver compound.

9. An antimicrobial latex composition according to claim 8, wherein said cationic natural rubber latex or said cationic synthetic polymer latex has solids content of about 20 to 70% by weight.

10. An antimicrobial latex composition according to claim 9, wherein said cationic natural rubber latex or said cationic synthetic polymer latex has solids content of about 30 to 65% by weight.

11. An antimicrobial latex composition according to claim 8, wherein said water-soluble silver compound is present in an amount of about 0.1 to 30% by weight, in terms of silver, based on the solids content of said latex.

12. An antimicrobial latex composition according to claim 11, wherein said water-soluble silver compound is present in an amount of about 0.5 to 10% by weight, in terms of silver, based on the solids content of said latex.

13. An antimicrobial latex composition according to claim 8, wherein said water-soluble silver compound is at least one compound selected from the group consisting of silver nitrate, silver chlorate, silver fluoride, silver lactate, and silver picrate.

14. An antimicrobial latex composition according to claim 8, wherein said latex has a pH value of about 1 to 5.

* * * * *